United States Patent
Lee et al.

(10) Patent No.: US 11,576,813 B2
(45) Date of Patent: Feb. 14, 2023

(54) THERMOTHERAPY BED

(71) Applicant: CERAGEM CO., LTD., Chungcheongnam-do (KR)

(72) Inventors: Dong Myoung Lee, Chungcheongnam-do (KR); Ho Sang Yu, Chungcheongnam-do (KR); Jin Cheol Park, Chungcheongnam-do (KR); Sang Ho Choi, Chungcheongnam-do (KR); Keun Young Paek, Chungcheongnam-do (KR)

(73) Assignee: CERAGEM CO., LTD., Chungcheongnam-Do (KR)

( * ) Notice: Subject to any disclaimer, the term of this patent is extended or adjusted under 35 U.S.C. 154(b) by 1052 days.

(21) Appl. No.: 16/321,865

(22) PCT Filed: Jan. 18, 2018

(86) PCT No.: PCT/KR2018/000856
§ 371 (c)(1),
(2) Date: Jan. 30, 2019

(87) PCT Pub. No.: WO2018/143587
PCT Pub. Date: Aug. 9, 2018

(65) Prior Publication Data
US 2019/0175393 A1 Jun. 13, 2019

(30) Foreign Application Priority Data
Feb. 1, 2017 (KR) .................. 10-2017-0014568

(51) Int. Cl.
*A61F 7/08* (2006.01)
*A47C 21/04* (2006.01)
(Continued)

(52) U.S. Cl.
CPC .............. *A61F 7/08* (2013.01); *A47C 19/128* (2013.01); *A47C 21/048* (2013.01);
(Continued)

(58) Field of Classification Search
CPC .......... A61F 7/08; A61F 7/0053; A61F 7/007; A61F 2007/0024; A47C 19/128;
(Continued)

(56) References Cited

U.S. PATENT DOCUMENTS

| 159,737 A | * | 2/1875 | York | A47B 2003/082 |
| | | | | 108/129 |
| 2,215,006 A | * | 9/1940 | Kovats | A47B 3/0812 |
| | | | | 108/126 |

(Continued)

FOREIGN PATENT DOCUMENTS

| CL | 201902156 | 7/2019 |
| CN | 2590595 | 12/2003 |

(Continued)

OTHER PUBLICATIONS

International Search Report and Written Opinion issued in International Patent Application No. PCT/KR2018/000856, dated May 8, 2018.

(Continued)

*Primary Examiner* — David R Hare
*Assistant Examiner* — Alison N Labarge
(74) *Attorney, Agent, or Firm* — Norton Rose Fulbright US LLP

(57) ABSTRACT

In order to maximize spatial utilization and to minimize the volume of a thermotherapy bed so that the thermotherapy bed can be easily stored or moved, the thermotherapy bed includes: a bed body having a thermotherapy device placed therein; side frames connected to both side surfaces of the bed body, respectively; and bed legs configured to support (Continued)

the bed body and connected to the side frames, respectively, wherein the thermotherapy device is placed in a center of the bed body and forms a protrusion on a bottom surface of the bed body, and the bed legs are folded to face an inside of the bed body and are accommodated in spaces formed at both sides of the thermotherapy device.

7 Claims, 4 Drawing Sheets

(51) Int. Cl.
    *A47C 19/12*      (2006.01)
    *A61F 7/00*      (2006.01)
    *A61H 39/06*      (2006.01)

(52) U.S. Cl.
    CPC ............ *A61F 7/0053* (2013.01); *A61H 39/06* (2013.01); *A61H 2201/0142* (2013.01); *A61H 2201/0161* (2013.01); *A61H 2201/0207* (2013.01); *A61H 2201/0221* (2013.01); *A61H 2201/0257* (2013.01); *A61H 2201/5082* (2013.01)

(58) Field of Classification Search
    CPC ....... A47C 21/048; A47C 19/04; A47C 21/04; A47C 21/044; A61H 39/08; A61H 2201/0142; A61H 2201/0161; A61H 2201/0207; A61H 2201/0221; A61H 2201/0257; A61H 2201/5058; A61G 7/00; A61G 7/05; A61G 2200/327
    See application file for complete search history.

(56) References Cited

U.S. PATENT DOCUMENTS

| | | | | |
|---|---|---|---|---|
| 2,898,837 | A * | 8/1959 | Scarselli | A47C 21/044 219/217 |
| 2,905,170 | A * | 9/1959 | Seaman | A61H 2201/014 601/57 |
| 3,725,966 | A * | 4/1973 | Blecker | A47C 19/128 5/202 |
| 2004/0194211 | A1 | 10/2004 | Friedman | |
| 2015/0238007 | A1 * | 8/2015 | Faller | A47B 3/0912 108/14 |

FOREIGN PATENT DOCUMENTS

| | | | |
|---|---|---|---|
| CN | 2829707 | 10/2006 | |
| CN | 102743249 | 10/2012 | |
| CN | 104644374 | 5/2015 | |
| DE | 202015106739 U1 * | 5/2016 | ............. A47B 3/087 |
| JP | 10258092 | 9/1998 | |
| JP | 3196532 U | 3/2015 | |
| KR | 20-0439871 | 5/2008 | |
| KR | 20110003953 | 4/2011 | |
| KR | 20120118398 | 10/2012 | |
| KR | 101452139 B1 * | 10/2014 | |
| KR | 10-2015-0053590 | 5/2015 | |
| KR | 20160115231 A * | 10/2016 | |
| RU | 2530791 | 10/2014 | |
| RU | 2577448 | 3/2016 | |
| RU | 2608235 | 1/2017 | |

OTHER PUBLICATIONS

Extended European Search Report issued in Corresponding European Application No. 18748551.1, dated Oct. 29, 2020.

Office Action issued in Corresponding Chinese Application No. 201710305364.4, dated Aug. 21, 2019 (English Translation provided).

Search Report issued in Corresponding Russian Application No. 2019125607, dated Jan. 15, 2021 (No. English translation provided).

Office Action Issued in Corresponding Chile Patent Application No. 2157-2019, dated Jun. 22, 2020.

* cited by examiner

THERMOTHERAPY BED

CROSS-REFERENCE TO RELATED APPLICATION

This application is a national phase application under 35 U.S.C. § 371 of International Application No. PCT/KR2018/000856, filed Jan. 18, 2018, which claims priority to and the benefit of Korean Patent Application No. 2017-0014568, filed on Feb. 1, 2017, the disclosures of which are each incorporated herein by reference in their entirety.

BACKGROUND

1. Field of the Invention

The present invention relates to a thermotherapy bed.

2. Discussion of Related Art

These days, thermotherapy beds that alleviate an acute or chronic pain generated in the muscle or nerve tissue of the spinal column due to a long-term work in the state of an improper position or habituation of this position, are moved along a user's body part so as to improve blood circulation of the body or remove instantaneous stiffness of muscles, and improve blood circulation by giving stimulus to a pain part by thermotherapy, have been widely used.

In thermotherapy beds according to the related art, a left side frame, a right side frame, a connecting frame that connects the left side frame to the right side frame, and a bed body disposed at an upper portion of the connecting frame are separately manufactured and assembled so that a thermotherapy bed can be manufactured. Thus, a manufacturing process is complicated, and manufacturing costs increase.

In addition, because bed legs of the thermotherapy bed are connected to the side frames and are maintained to be always fixed thereto, when the thermotherapy bed is not used, i.e., when the thermotherapy bed is stored or moved, due to a space of the thermotherapy bed, the thermotherapy bed cannot be easily stored or moved.

SUMMARY OF THE INVENTION

The present invention is directed to a thermotherapy bed, whereby a manufacturing process can be simplified and manufacturing costs can be reduced.

The present invention is also directed to a thermotherapy bed, whereby spatial utilization is maximized and the volume of the thermotherapy bed is minimized so that the thermotherapy bed can be easily stored or moved.

According to an aspect of the present invention, there is provided a thermotherapy bed including: a bed body having a thermotherapy device placed therein; side frames connected to both side surfaces of the bed body, respectively; and bed legs configured to support the bed body and connected to the side frames, respectively, wherein the thermotherapy device is placed in a center of the bed body and forms a protrusion on a bottom surface of the bed body, and the bed legs are folded to face an inside of the bed body and are accommodated in spaces formed at both sides of the thermotherapy device.

The thermotherapy bed may further include folding portions configured to connect the bed legs to the side frames, respectively.

The folding portions may include stoppers configured to prevent the bed legs from being deviated from an outside of the bed body when the bed legs are unfolded to face the outside of the bed body.

The folding portions may further include first fixing portions configured to fix the bed legs when the bed legs are unfolded to face the outside of the bed body.

When the bed legs are folded to face the inside of the bed body, bottom surfaces of the bed legs and a bottom surface of the thermotherapy device may form a same plane.

When the bed legs are unfolded to face the outside of the bed body, one side surface of the side frames and one side surface of the bed legs may form a same plane.

The thermotherapy bed may further include: second fixing portions provided on one end of each of the bed legs; and third fixing portions provided on both ends of the thermotherapy device, respectively, and fastened to the second fixing portions to fix the bed legs, respectively, when the bed legs are folded to face the inside of the bed body.

The second fixing portions may be projections provided inside the bed legs, and the third fixing portions may be concave portions with concave shapes in a downward direction of the bed body.

The second fixing portions may be concave portions provided inside the bed legs, and the third fixing portions may be projections with convex shapes in the downward direction of the bed body.

The projections may be tightly fitted into the concave portions to fix the bed legs, respectively.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
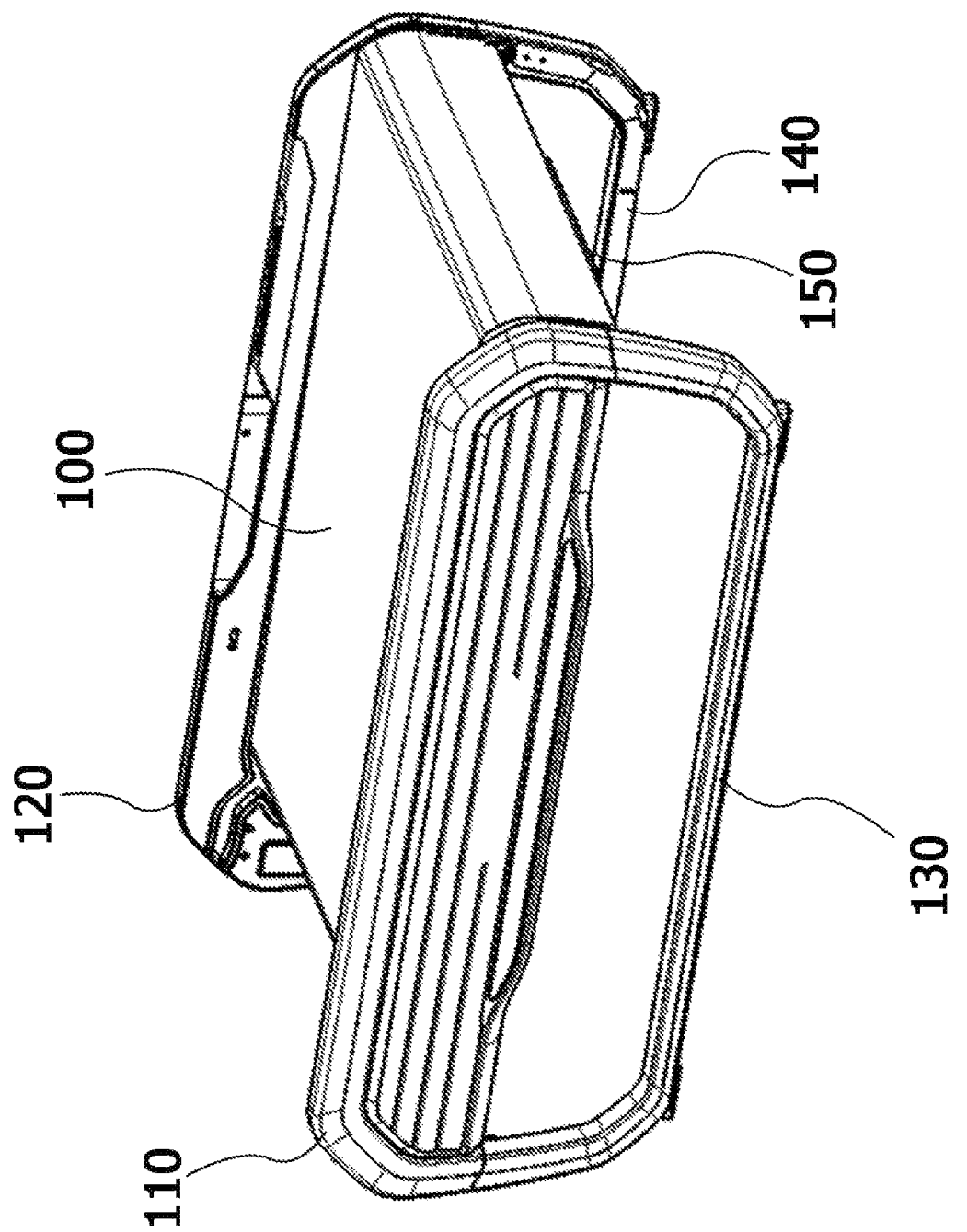
FIG. 1 is a perspective view of a thermotherapy bed when bed legs are unfolded, according to an embodiment of the present invention.

Exemplary embodiments of the present invention will be described in detail below with reference to the accompanying drawings so that those skilled in the art can easily embody the invention. The invention can be embodied in several different forms and is not limited to embodiments that will be described below. In the drawings, for clarity, irrelevant portions to descriptions are omitted, and the same reference numerals throughout the specification are used for the same or similar components or elements.

In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Figure 2:
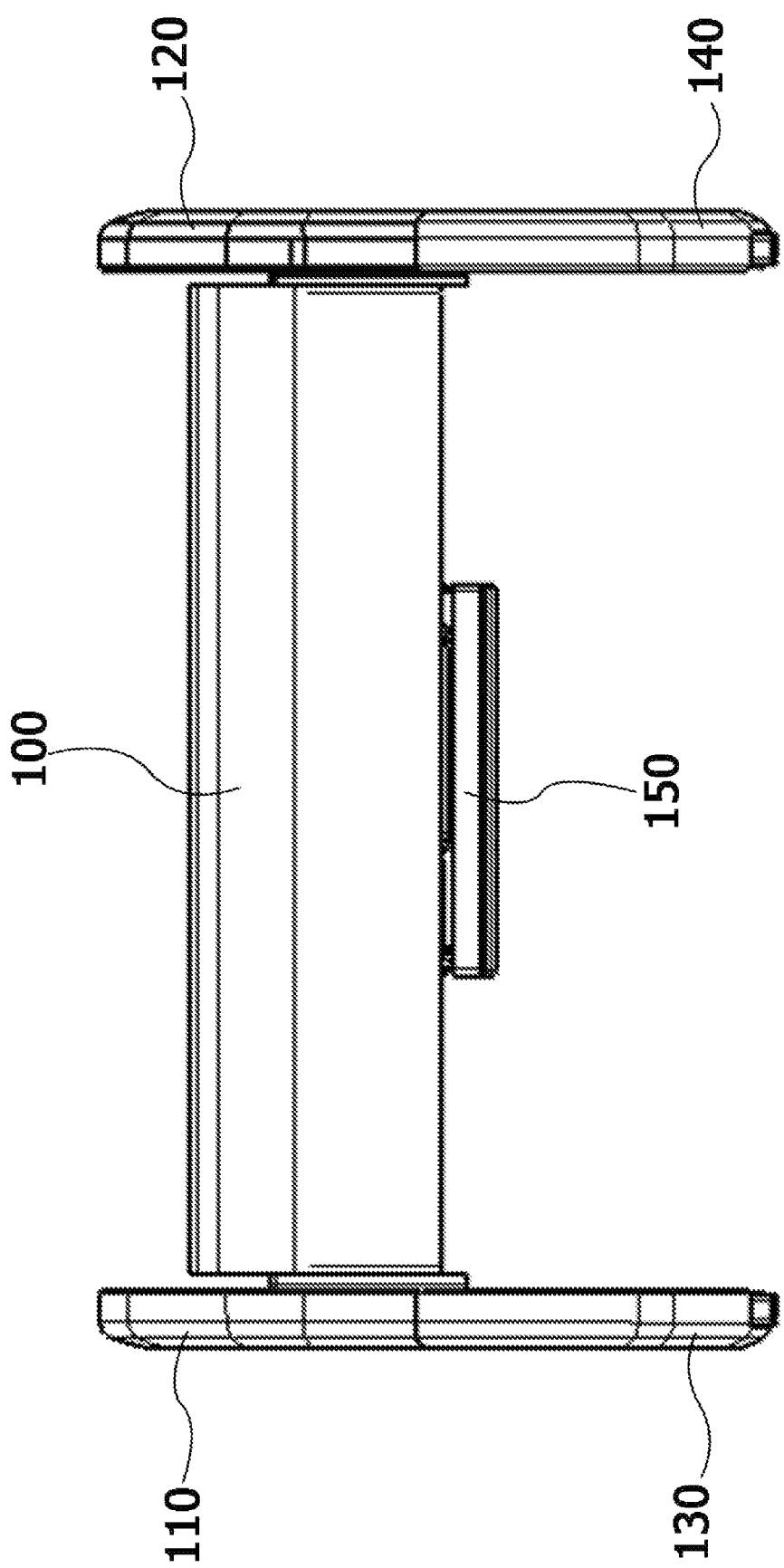
FIG. 2 is a side view of the thermotherapy bed when the bed legs are unfolded, according to an embodiment of the present invention.

FIG. 1 is a perspective view of a thermotherapy bed when bed legs are unfolded, according to an embodiment of the present invention, and FIG. 2 is a side view of the thermotherapy bed when the bed legs are unfolded, according to an embodiment of the present invention.

Figure 3:
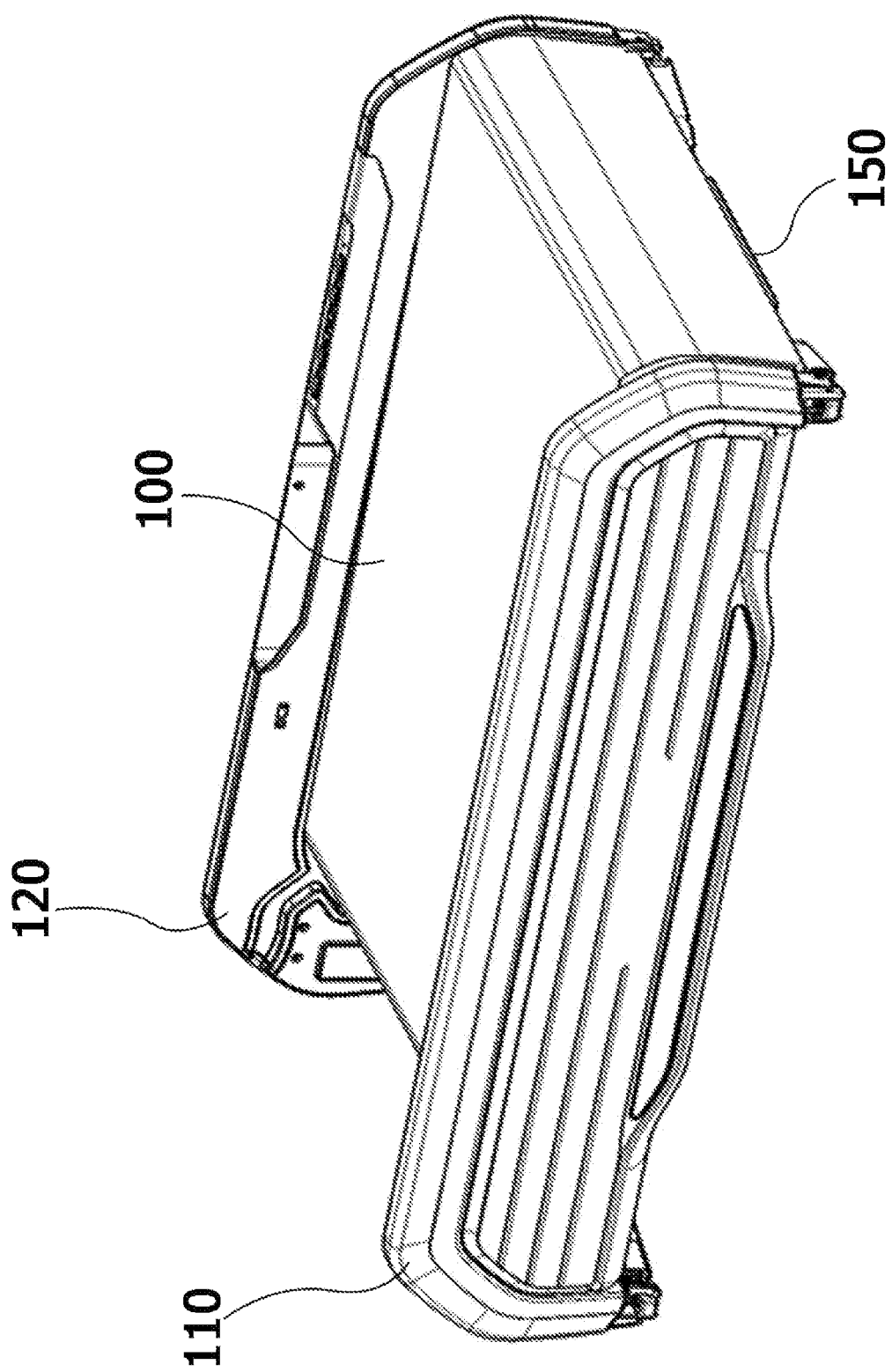
FIG. 3 is a perspective view of the thermotherapy bed when the bed legs are folded, according to an embodiment of the present invention.
Figure 4:
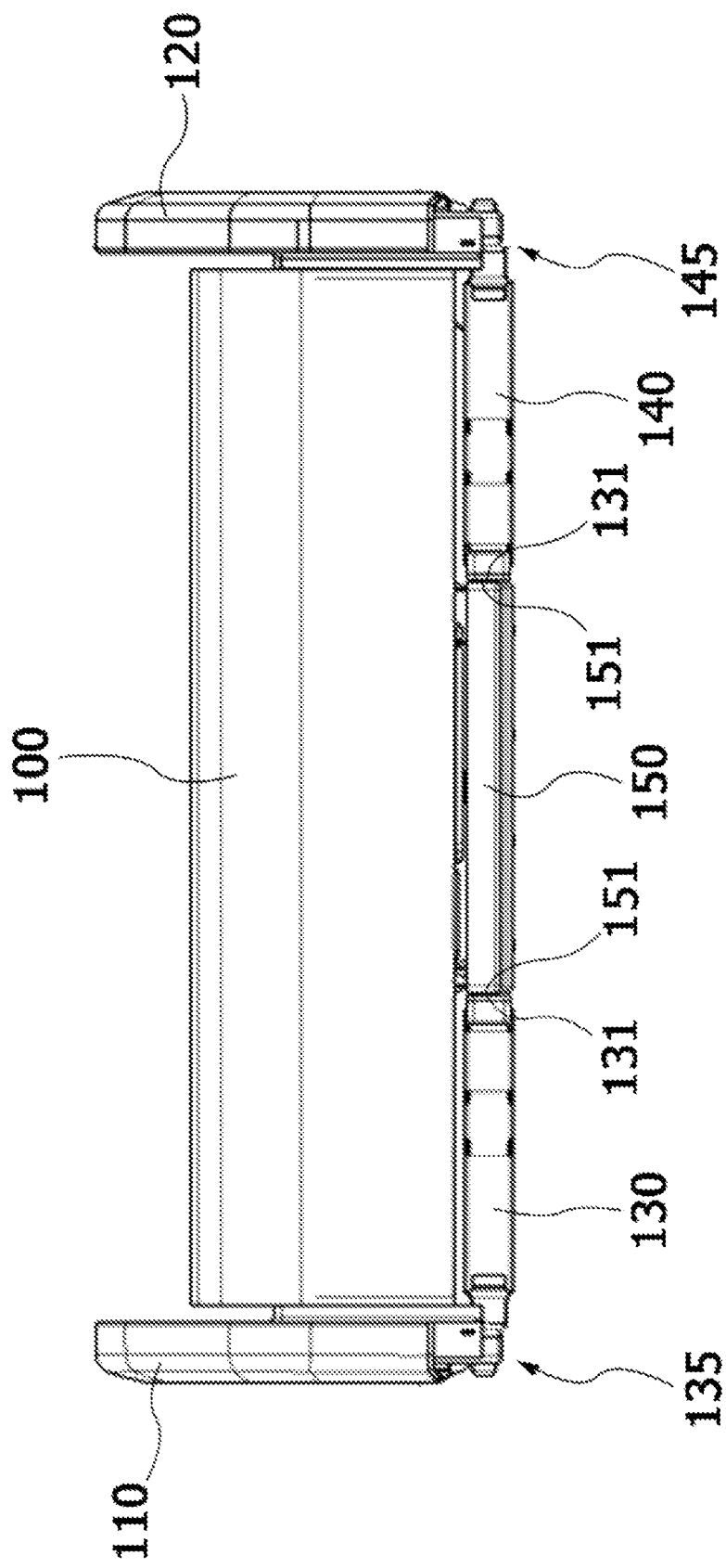
FIG. 4 is a side view of the thermotherapy bed when the bed legs are folded, according to an embodiment of the present invention.

FIG. 3 is a perspective view of the thermotherapy bed when the bed legs are folded, according to an embodiment of the present invention, and FIG. 4 is a side view of the thermotherapy bed when the bed legs are folded, according to an embodiment of the present invention.

As illustrated in FIGS. 1 through 4, the thermotherapy bed according to an embodiment of the present invention may include a bed body 100, side frames 110 and 120, and bed legs 130 and 140.

A thermotherapy device 150 is provided inside the bed body 100 in a longitudinal direction of the bed body 100. The thermotherapy device 150 moves along a user's body part when the user lies down on the bed body 100 and gives stimulus to a pain part by thermotherapy so as to improve blood circulation.

In detail, the thermotherapy device 150 may include a ceramic member (not shown), a transfer unit (not shown), and a sensor unit (not shown).

Here, the ceramic member has a heating member placed therein and is moved by the transfer unit in the longitudinal direction of the bed body 100 and is in contact with the user's body portion, thereby performing a massage function and a moxibustion function through supply of heat.

Also, the sensor unit may include a sensor and a scanner and may sense the user's body information when a massage or moxibustion work is performed, so that the ceramic member can perform a user-customized massage or moxibustion work.

Although not shown, the bed body 100 may include a lower bed body and an upper bed body. In this case, the upper bed body may slide into the lower bed body to be unfolded or overlap the lower bed body.

In this way, when the thermotherapy bed is not used, the upper bed body slides into the lower bed body so as to overlap the lower bed body such that spatial utilization can be easily made.

As illustrated in FIGS. 1 and 2, the side frames 110 and 120 include a left side frame 110 and a right side frame 120 and are connected to both side surfaces of the bed body 100, respectively. The bed legs 130 and 140 include a left bed leg 130 and a right bed leg 140 and are connected to the side frames 110 and 120, respectively, to support the bed body 100.

Also, the bed legs 130 and 140 may include four legs that extend from both sides of the left side frame 110 and the right side frame 120. However, in order to more solidly support the bed body 100, the left bed leg 130 and the right bed leg 140 may be connected to each other while corresponding to a support surface.

Meanwhile, in the thermotherapy bed according to an embodiment of the present invention, the bed body 100 and the side frames 110 and 120 may be integrally formed.

Thus, a manufacturing process can be simplified compared to a process of manufacturing an existing thermotherapy bed in which side frames, a connecting frame that connects the side frames to each other and a bed body disposed at an upper portion of the connecting frame are separately manufactured and assembled, and manufacturing costs can be reduced.

As illustrated in FIGS. 2 and 4, the thermotherapy device 150 is placed in a center of the bed body 100 to form a protrusion on a bottom surface of the bed body 100. Thus, spaces are formed at both sides of the bed body 100 in which the thermotherapy device 150 is not placed.

Here, as illustrated in FIGS. 3 and 4, in the thermotherapy bed according to an embodiment of the present invention, by using such spaces, when the thermotherapy bed is used, the bed legs 130 and 140 are unfolded to support the bed body 100, and when the thermotherapy bed is not used, for example, when the thermotherapy bed is stored or moved, the bed legs 130 and 140 may be folded and accommodated in the spaces formed at both sides of the bed body 100.

In this case, lengths of the bed legs 130 and 140 may be the same as widths of the spaces formed at both sides of the bed body 100 in which the thermotherapy bed 150 is not placed.

That is, as illustrated in FIG. 4, the bed legs 130 and 140 of the thermotherapy bed according to an embodiment of the present invention may be folded to face an inside of the bed body 100 and accommodated in spaces formed at both sides of the thermotherapy device 150.

Thus, when the thermotherapy bed is stored or moved, the volume of the thermotherapy bed may be minimized such that the thermotherapy bed can be easily stored or moved.

Meanwhile, when the bed legs 130 and 140 are folded to face the inside of the bed body 100, bottom surfaces of the bed legs 130 and 140 and a bottom surface of the thermotherapy device 150 may form the same plane.

For example, the bed legs 130 and 140 may be folded at approximately 90° and may have the same widths as that of the protrusion formed on the bottom surface of the bed body 100.

Thus, when the thermotherapy bed having the bed legs 130 and 140 folded is placed on the floor so as to be stored or moved, the thermotherapy bed may be parallel to the floor surface. Thus, the thermotherapy bed can be more easily stored or moved.

In addition, as illustrated in FIGS. 1 and 2, the bed legs 130 and 140 may be unfolded at approximately 90°, and when the bed legs 130 and 140 are unfolded to face an outside of the bed body 100, one side surface of the side frames 110 and 120 and one side surface of the bed legs 130 and 140 may form the same plane.

Thus, when the bed legs 130 and 140 are unfolded so that the user is able to use the thermotherapy bed, the bed legs 130 and 140 may support the bed body 100 more solidly.

In addition, as illustrated in FIG. 4, the thermotherapy bed according to an embodiment of the present invention may further include folding portions 135 and 145 that are capable of folding/unfolding the bed legs 130 and 140 by connecting the bed legs 130 and 140 to the side frames 110 and 120, respectively.

The folding portions 135 and 145 may include stoppers (not shown) and first fixing portions (not shown).

Here, the stoppers prevent the bed legs 130 and 140 from being deviated from the outside of the bed body 100 when the bed legs 130 and 140 are unfolded to face the outside of the bed body 100.

The first fixing portions fix the bed legs 130 and 140 so as to prevent the bed legs 130 and 140 from being folded again when the bed legs 130 and 140 are unfolded to face the outside of the bed body 100.

Also, the thermotherapy bed according to an embodiment of the present invention may further include second fixing portions (131) and third fixing portions (151) so as to prevent the bed legs 130 and 140 from being unfolded again when the thermotherapy bed is stored or moved in a state in which the bed legs 130 and 140 are folded.

Here, the second fixing portions are provided on one end of each of the bed legs 130 and 140, and the third fixing portions are provided on both ends of the thermotherapy device 150 and are fastened to the second fixing portions so as to fix the bed legs 130 and 140, respectively, when the bed legs 130 and 140 are folded to face the inside of the bed body 100.

For example, the second fixing portions may be projections provided inside the bed legs 130 and 140, and the third fixing portions may be concave portions with concave shapes in a downward direction of the bed body 100. In this case, the projections may be tightly fitted into the concave portions to fix the bed legs 130 and 140, respectively.

Contrary to this, the second fixing portions may be concave portions provided inside the bed legs 130 and 140, and the third fixing portions may be projections with convex shapes in the downward direction of the bed body 100. In this case, the projections may be tightly fitted into the concave portions to fix the bed legs 130 and 140, respectively.

Thus, in the thermotherapy bed according to an embodiment of the present invention, the bed legs 130 and 140 can be prevented from being unfolded again when the thermotherapy bed is stored or moved in a state in which the bed legs 130 and 140 are folded.

As described above, according to the present invention, a manufacturing process can be simplified compared to a process of manufacturing an existing thermotherapy bed in which side frames, a connecting frame that connects the side frames to each other and a bed body disposed at an upper portion of the connecting frame are separately manufactured and assembled, and manufacturing costs can be reduced.

In addition, according to the present invention, in order to maximize spatial utilization, bed legs are folded to face an inside of a bed body and are accommodated in spaces formed at both sides of a thermotherapy device so that the volume of the thermotherapy bed can be minimized when the thermotherapy bed is stored or moved and the thermotherapy bed can be easily stored or moved.

Furthermore, according to the present invention, when the thermotherapy bed having the bed legs folded is placed on the floor so as to be stored or moved, the thermotherapy bed is parallel to a floor surface so that the thermotherapy bed can be more easily stored or moved.

While the present invention has been described with reference to exemplary embodiments thereof, it will be apparent to those skilled in the art that various modifications can be made to the above-described exemplary embodiments of the present invention without departing from the essential features of the invention. Thus, the exemplary embodiments should be considered in descriptive sense only and not for purposes of limitation, and the scope of the technical spirit of the present invention is not limited thereto. Therefore, the scope of the invention is defined not by the detailed description of the invention but by the appended claims, and it is intended that the present invention covers all such modifications provided they come within the scope of the appended claims and their equivalents.

What is claimed is:

1. A thermotherapy bed comprising:
a bed body having a thermotherapy device placed therein;
side frames connected to both side surfaces of the bed body, respectively; and
bed legs configured to support the bed body and connected to the side frames, respectively,
wherein the thermotherapy device is placed in a center of the bed body and forms a protrusion on a bottom surface of the bed body, and the bed legs are folded to face an inside of the bed body and are accommodated in spaces formed at both sides of the thermotherapy device,
wherein the thermotherapy bed is configured so that when the bed legs are folded to face the inside of the bed body and the bed body is put down on a floor, the bottom surface of the thermotherapy device and the bed legs are in contact with the floor to maintain a balance of the bed body.

2. The thermotherapy bed of claim 1, further comprising folding portions configured to connect the bed legs to the side frames, respectively.

3. The thermotherapy bed of claim 2, wherein the folding portions include stoppers configured to prevent the bed legs from being deviated from an outside of the bed body when the bed legs are unfolded to face the outside of the bed body.

4. The thermotherapy bed of claim 2, wherein the folding portions further include first fixing portions configured to fix the bed legs when the bed legs are unfolded to face an outside of the bed body.

5. The thermotherapy bed of claim 1, wherein, when the bed legs are folded to face the inside of the bed body, bottom surfaces of the bed legs and a bottom surface of the thermotherapy device form a same plane.

6. The thermotherapy bed of claim 1, wherein, when the bed legs are unfolded to face an outside of the bed body, one side surface of the side frames and one side surface of the bed legs form a same plane.

7. The thermotherapy bed of claim 1, further comprising:
second fixing portions provided on one end of each of the bed legs; and
third fixing portions provided on both ends of the thermotherapy device, respectively, and fastened to the second fixing portions to fix the bed legs, respectively, when the bed legs are folded to face the inside of the bed body.

* * * * *